United States Patent
Kusters et al.

(10) Patent No.: US 9,116,090 B2
(45) Date of Patent: Aug. 25, 2015

(54) METHOD AND DEVICE FOR PREPARING TISSUE AND MOULD FOR PRETREATING TISSUE MATERIAL

(75) Inventors: Ronald Johannes Wilhelmus Kusters, Almere (NL); Maricus Johannes Van Dijk, Elsendorp (NL)

(73) Assignee: Klinipath B.V., Duiven (NL)

( * ) Notice: Subject to any disclaimer, the term of this patent is extended or adjusted under 35 U.S.C. 154(b) by 472 days.

(21) Appl. No.: 13/267,093

(22) Filed: Oct. 6, 2011

(65) Prior Publication Data
US 2013/0087945 A1    Apr. 11, 2013

(30) Foreign Application Priority Data
Oct. 6, 2010   (NL) ...................................... 2005461

(51) Int. Cl.
*A61B 10/00*    (2006.01)
*G01N 1/36*    (2006.01)
*G01N 1/31*    (2006.01)

(52) U.S. Cl.
CPC ............ *G01N 1/36* (2013.01); *G01N 2001/315* (2013.01); *G01N 2001/366* (2013.01)

(58) Field of Classification Search
CPC .................................. G01N 1/06; G01N 1/36
USPC ......................................................... 422/536
See application file for complete search history.

(56) References Cited

U.S. PATENT DOCUMENTS

| | | | |
|---|---|---|---|
| 5,269,671 A | 12/1993 | McCormick | |
| 5,968,436 A | 10/1999 | Takezaki | |
| 7,722,810 B2 * | 5/2010 | Allen et al. | ..................... 422/63 |
| 2008/0254504 A1 | 10/2008 | Vom et al. | |
| 2011/0171088 A1 | 7/2011 | Takahashi | |

FOREIGN PATENT DOCUMENTS

| | | |
|---|---|---|
| WO | 2006/060317 A1 | 6/2006 |
| WO | 2009/152575 A1 | 12/2009 |

OTHER PUBLICATIONS

Search Report and Written Opinion from corresponding Dutch Application No. NL 2005461 dated May 23, 2011.

* cited by examiner

*Primary Examiner* — Jyoti Nagpaul
(74) *Attorney, Agent, or Firm* — Renner, Otto, Boisselle & Sklar, LLP (57) ABSTRACT

The invention relates to a method for preparing tissue material. The method comprises placing a quantity of tissue material in a closable but liquid-permeable assembly of a mold and enclosing element, enclosing the tissue material, guiding the tissue material placed in the receiving space at least through a hydrophilic liquid such as an alcohol solution, wherein water is extracted from the tissue material; and embedding the tissue material placed in the receiving space by at least partially filling the receiving space with a matrix material; wherein the assembly of mold and enclosing element has an orientation relative to a reference direction, and the orientation in one treatment step differs from the orientation in another treatment step. The invention also relates to a device and mold for performing the method.

12 Claims, 6 Drawing Sheets

METHOD AND DEVICE FOR PREPARING TISSUE AND MOULD FOR PRETREATING TISSUE MATERIAL

TECHNICAL FIELD

The invention relates to a method and device for preparing tissue material. The invention also relates to a mould for treating tissue material and an assembly of such a mould and an enclosing element. The invention further relates to a method and device for extracting water from tissue material and embedding tissue material with a matrix material in one operation.

BACKGROUND

The study of tissue material takes place on a large scale for histological or pathological testing, such as for the purpose of making a diagnosis. Tissue is understood here to mean organic material isolated from, for instance, humans, animals or plants. For the purpose of studying the tissue material, the tissue material is cut into thin sections. By subsequently mounting the tissue cut into sections on slides, the tissue material can be studied under a microscope. However, such isolated tissue material comprises a substantial quantity of water. This makes cutting of the tissue material into sections difficult and increases the risk of undesirable variations in the thickness of the sections. There is also the risk during cutting of the tissue material into sections that the tissue material is compressed, thus reducing the reliability of the results of the study of the tissue.

In order to obviate the above stated drawbacks, it is known to pretreat the tissue material before it is cut into sections. Sample preparation prepares tissue specimens for sectioning, staining and diagnosis. The known paraffin processing method moves tissue specimens through a series of steps that comprise a fixation step aiming to preserve the tissue; a pretreatment step that removes water from the specimen by submersing it in, for instance, ethanol, clearing the tissue by contact with a clearing agent such as xylene, and infiltrating the tissue with paraffin wax; and an embedding step that allows orientation of the specimen in a block of paraffin or other moulding fluid. A final sectioning step using a microtome produces very thin sections from the block, which sections are positioned on a microscope slide for staining.

In the pretreatment step, the tissue material is placed in a container permeable to the relevant liquids and brought into contact with the different liquids. A known device for pretreating tissue material is described for instance in US 2011/0171088 A1. Such an apparatus (known in the art as a tissue processor) comprises a tissue treatment chamber connected to a number of containers for different pretreatment liquids such as alcohols, xylene and paraffin. Tissue material is arranged in a container permeable to the liquids and placed in the tissue treatment chamber, wherein the liquids flow sequentially through the tissue treatment chamber and the tissue material is brought into contact with these liquids.

For the purpose of embedding in a matrix material the pretreated tissue material infiltrated with paraffin, according to the known method, the tissue material is taken out of the permeable container and placed in a mould. A known mould here comprises a housing provided with a receiving space for the tissue material and an opening for placing the tissue into the receiving space. A known mould for embedding is described in WO 2009/152575 A1 and comprises, in addition to the housing and the receiving space, a container permeable to paraffin which functions as cover for the housing. After placing of the tissue material in the receiving space, the receiving space is closed with the cover or cassette and the whole is treated in a separate embedding device, which is likewise described in WO 2009/152575 A1. Following embedding of the mould, tissue material and cover in a matrix material, the mould is removed, wherein the cover remains to which is connected a projection in the form of the receiving space and comprising the tissue material. Diverse matrix materials are suitable for embedding purposes. The only prerequisite is that the matrix material can be brought from a first state, in which the matrix material is fluid for the purpose of embedding the tissue material through penetration of the matrix material into the tissue material, to a second state in which the matrix material is cuttable. A suitable matrix material is paraffin. In the cuttable state the tissue is cut into sections, mounted on a glass slide and the tissue material is ready to be studied. During cutting into sections, the embedded tissue material is secured with the cover in the microtome apparatus.

The above described known method for preparing tissue material is relatively labour-intensive and involves the risk of the tissue material being unnecessarily damaged during removal of the pretreated tissue material from the container and placing thereof in a mould. Tissue material can also be undesirably exchanged with tissue material from another container, thus reducing the reliability of the origin of the tissue material. It is further of great importance that the tissue material is placed in the correct orientation in the mould.

There is therefore a need for a method and device for preparing tissue material wherein the above stated drawbacks are at least partially obviated. An object of the present invention is to provide for the above stated need.

SUMMARY

The invention provides for this purpose a method for preparing tissue material, comprising the steps of:

A) providing an assembly of a mould and an enclosing element coupled thereto, wherein the mould comprises a housing provided with a receiving space for the tissue material and an opening for placing the tissue material into the receiving space, and coupling means for coupling the enclosing element to the mould, the enclosing element being adapted for enclosing the tissue material liquid-permeably in the receiving space;

B) placing a quantity of tissue material in the receiving space of the mould;

C) liquid-permeably enclosing the quantity of tissue material placed in the receiving space by moving the enclosing element into a closing position, wherein displacement of tissue material placed in the receiving space through the opening and outside the receiving space is prevented;

D) guiding the tissue material placed in the receiving space at least through a hydrophilic liquid such as an alcohol solution, wherein water is extracted from the tissue material; and E) embedding the tissue material placed in the receiving space by at least partially filling the receiving space with a matrix material;

wherein the assembly of mould and enclosing element has an orientation relative to a reference direction, and the orientation in step D) differs from the orientation in step E).

The method according to the invention makes it possible to pretreat tissue material, such as for instance by extracting water from tissue material placed in the receiving space of the mould, after which the pretreated tissue material can be immediately embedded in a matrix material. It is not necessary here to take the tissue material out of a separate liquid-permeable container and place it in a likewise separate mould. This is because the mould applied in the method according to the invention makes it possible to pretreat the tissue material placed in the receiving space in that the tissue material is enclosed liquid-permeably and the orientation of the assembly of mould and enclosing element can be changed. Because the pretreatment and the embedding of the tissue material are performed consecutively, the method for preparing tissue material is less labour-intensive than the known method, and particularly the risk of tissue material being unnecessarily damaged and/or tissue material being exchanged are reduced.

According to an embodiment, enclosing of tissue material placed in the receiving space comprises of coupling a liquid-permeable wall part to the mould and displacing the wall part into a position substantially closing the opening liquid-permeably. A quantity of tissue material to be studied is hereby enclosed in simple manner in the mould.

The invention also provides a device for preparing tissue material, comprising a liquid container and a carrier for carrying in the liquid container at least one assembly of a mould and an enclosing element as described above coupled thereto, wherein the device is adapted to vary the level of the liquid in the liquid container and to adjust the orientation of the carrier in the liquid container. By varying the orientation of the carrier relative to a reference direction, for instance the horizontal direction, the orientation of assemblies of mould and enclosing element received in the container is likewise varied. The device according to the invention makes it possible to guide a plurality of pretreatment liquids, such as for instance a hydrophilic liquid, through the tissue material, wherein air that is possibly present can escape from the mould. For the purpose of varying the liquid level in the container the device can for instance comprise a pump for pumping liquid into and/or out of the container. The device can also comprise a feed debouching into the container for raising the liquid level by feeding liquid into the container and a discharge preferably located in or close to a bottom of the container and debouching into the container for lowering the liquid level in the container by discharging liquid through the discharge.

In an embodiment, the device is adapted to translate liquid held in the liquid container and the carrier relative to each other. The tissue material and the liquid can hereby be displaced relative to each other, whereby not only can the contact surface of the tissue material be enlarged but whereby liquid which has already been brought into contact with the tissue material is also forced out of the tissue material and brought into contact with liquid which has not yet been brought into contact with the tissue material. If the liquid is hydrophilic liquid, water can hereby be extracted from the tissue material in a more efficient manner, i.e. within a shorter period of time.

Using the device according to the invention, tissue material can be guided through different pretreatment liquids such as a hydrophilic liquid, xylene, paraffin and the like by placing the assembly of mould and enclosing element in the liquid container, wherein the mould is provided in the receiving space thereof with tissue material which is held enclosed, and repeatedly lowering and raising the level of the pretreatment liquid in the container such that the tissue material repeatedly lies respectively substantially above and below the level of the pretreatment liquid, wherein during lowering and raising of the level of the pretreatment liquid in the container the receiving space of the mould respectively faces at least partially downward and upward. Pretreatment liquid is hereby guided through the tissue material, wherein air that is possibly present can escape easily from the mould.

In a further preferred embodiment, a method is provided in which the orientation of the assembly of mould and enclosing element is oblique relative to the horizontal direction when the level of the pretreatment liquid in the container is raised. Oblique is understood to mean that the assemblies of mould and closing element are oriented at an angle differing from zero relative to the horizontal direction. The oblique angle preferably amounts to more than 45°, and more preferably more than 60°. Air present in the tissue material can in this way escape relatively easily during filling of the liquid container.

In yet another preferred embodiment, a method is provided in which the orientation of the assembly of mould and enclosing element is substantially vertical relative to the horizontal direction when the level of the pretreatment liquid in the container is lowered. Pretreatment liquid still present in the tissue material or mould can in this way escape relatively easily during draining of the liquid container.

In yet another preferred embodiment, a method is provided in which the orientation of the assembly of mould and enclosing element is substantially horizontal when performing step E) wherein the receiving space is filled with a matrix material and the tissue material placed in the receiving space is embedded. For this purpose the level of the matrix material in the container is raised to a height at which this matrix material can flow into the mould. Matrix material present in the tissue material or mould is in this way retained during draining of the liquid container.

The method and device according to the invention make it possible to improve the pretreatment and embedding of tissue material in a matrix material suitable for the purpose. The risk of air being present in, or in the immediate vicinity of, the tissue material from which water has been removed is also reduced, thereby reducing the risk of tissue material being damaged, particularly during cutting of embedded tissue material into sections.

The device according to the invention makes use of a carrier in which a number of assemblies of mould and enclosing element are received. The carrier is rotatable about a preferably horizontal shaft. In order to ensure that, during the different operations wherein the carrier can be placed in different oriented positions relative to the horizontal direction, tissue material received in the mould cannot escape but the pretreatment liquids and the matrix material can nevertheless flow properly therethrough, the invention provides for this purpose a mould with coupling means which are adapted to couple an enclosing element to the mould for enclosing the tissue liquid-permeably in the receiving space for the purpose of preventing displacement of tissue material held in the receiving space through the opening and outside the receiving space.

The coupling means can take very diverse forms. The coupling means can for instance comprise a band manufactured from elastic material which can be coupled to the housing such that tissue material placed in the receiving space is enclosed under bias. In an embodiment the coupling means comprise at least one coupling element adapted to couple the enclosing element to the mould in co-action with at least one counter-coupling element forming part of the enclosing element. A quantity of tissue material to be studied can hereby be enclosed in simple manner in the mould. Because the enclosing element encloses the tissue material liquid-permeably in the receiving space, the tissue material placed in the receiving space can be brought into contact with hydrophilic liquid, whereby water can be extracted from the tissue material. It is noted here that liquid-permeable is understood to mean that, while liquid can displace through the wall part, the tissue material cannot do so. The enclosing element can for instance comprise a wall part here which is provided with a plurality of through-openings in distributed arrangement.

Although a coupling element adapted to couple the enclosing element in only one position to the mould is not precluded, in another embodiment the at least one coupling element is adapted to couple the enclosing element to the mould for displacement between a first position leaving the opening substantially clear and a second position substantially closing the opening liquid-permeably. A quantity of tissue material can hereby easily be placed in the receiving space in the position of the enclosing element leaving the opening substantially clear, after which the tissue material placed in the receiving space is enclosed in the receiving space by displacing the enclosing element to a position substantially closing the opening liquid-permeably. Because the enclosing element is coupled to the mould during displacing of the enclosing element to a position substantially closing the opening liquid-permeably, the risk of undesirable displacement of the enclosing element during placing of the tissue material in the receiving space is reduced.

In another embodiment, the coupling means comprise a first coupling element and a second coupling element located at a distance from the first coupling element for coupling the enclosing element to the mould at two coupling positions lying at a mutual distance in co-action with a first counter-coupling element forming part of the enclosing element and a second counter-coupling element located at a distance from the first coupling element. A reliable method of coupling the enclosing element to the mould is hereby obtained. This reduces the risk of the enclosing element coupled to the mould detaching from the mould.

For unambiguous positioning of the wall part in a position substantially closing the opening liquid-permeably, the mould comprises a stop which is adapted to limit the displacement of a wall part coupled to the mould in a position substantially closing the opening liquid-permeably. This increases the reliability with which the tissue material is enclosed in the receiving space. Enclosing tissue displaceably in the receiving space is not precluded. If it is the wish however to enclose tissue under bias in the receiving space and multiple individual pieces of tissue material have to be tested, wherein the individual pieces of tissue material have predetermined dimensions, the bias with which individual pieces of tissue material placed in the receiving spaces is held substantially constant. The individual pieces of tissue material are hereby prepared in a more uniform manner.

A simple coupling of the enclosing element to the mould is obtained when the housing comprises on a first side of the mould a first standing wall extending from the stop, wherein the first standing wall is provided at the free end thereof with a first coupling element formed as a flange, and comprises on a second side of the mould opposite the first side a second standing wall extending from the stop and formed as second coupling element, wherein the second standing wall encloses an angle with the stop. The enclosing element is coupled to the mould by placing the enclosing element between the flange and the stop and between the second standing wall and the stop. The first standing wall and the flange provided at the free end thereof and the second standing wall are preferably formed such that the enclosing element and/or the flange and/or the second standing wall have to be deformed, whereby the enclosing element is coupled in locking manner to the mould.

Although the tissue material can be brought into contact to sufficient extent with a hydrophilic liquid for extracting water from the tissue material when the housing of the mould is not given a liquid-permeable form, in another embodiment, a wall of at least the receiving space of the housing of the mould is liquid-permeable. Bringing into contact the tissue material from which water has to be extracted is hereby improved, since during guiding of the tissue material through the hydrophilic liquid a flow of the hydrophilic liquid is obtained through the mould and along the tissue material. It is advantageous here for a wall of the receiving space of the housing opposite the opening of the housing to be liquid-permeable. During guiding of the tissue material through the hydrophilic liquid a good throughflow of the hydrophilic liquid along and through the tissue material is hereby obtained, whereby extraction of water from the tissue material takes place efficiently, i.e. homogeneously and in a relatively short period of time.

When a wall of at least the receiving space of a housing takes a liquid-permeable form, the liquid-permeable part of the housing can be adapted for the purpose of embedding the tissue material with a matrix material so that no liquid is allowed through. The liquid-permeable part of the housing can for instance thus be covered with a (substantially) liquid-blocking covering, such as an optionally self-adhesive film. In an embodiment the liquid-permeable wall of the housing is adapted to allow passage of a hydrophilic liquid for extracting water from tissue material placed in the receiving space and to block matrix material in the liquid state for embedding tissue material placed in the receiving space. The mould can hereby be used without further modifications to extract water from the tissue material by guiding the tissue through a hydrophilic liquid as well as to embed with a matrix material the tissue material from which water has been removed. The matrix material will after all have a higher viscosity than the hydrophilic liquid, whereby the hydrophilic liquid is allowed through the housing but the matrix material will be held back by the liquid-permeable wall parts.

The mould can be manufactured from diverse materials. It is desirable here that at least the part of the housing of the mould enclosing the receiving space is to a certain extent inert so that it does not affect the properties of the tissue material to be studied, or at least only does so to slight extent. If it is desired that the hydrophilic liquid and/or the matrix material have a predetermined increased temperature, it is desirable that the properties of the material from which the mould is manufactured are not affected, or at least affected to limited extent, by this higher temperature. An example of a higher temperature is 60° C., at which paraffin is liquid. In an embodiment the mould is manufactured substantially from a material selected from the group consisting of: metal, metal alloy, in particular steel, steel alloy, aluminium, aluminium alloy, plastic and combinations thereof. Such materials combine good strength and inertness and can be readily processed.

In a further embodiment, the mould comprises a retainer for tissue material placed in the receiving space, wherein the retainer is manufactured from flexible material cuttable with a microtome and wherein at least during preparation and study of tissue material the material is resistant to stains, solvents and chemicals used for preparing tissue material. A user can thus place the tissue material at a desired location in the receiving space. There is a risk here of the tissue material being placed at an undesirable location during placing thereof in the mould and/or due to embedding thereof in a matrix material. Because the retainer is cuttable with a microtome, the assembly of tissue material, retainer and matrix material can be taken as a whole out of the receiving space and cut into sections using a microtome. A microtome is an apparatus with which very thin slices can be cut very precisely for the purpose of making microscopic preparations.

In an advantageous embodiment the retainer is adapted to hold tissue material in a predetermined orientation. A user can hereby place tissue material in the receiving space of the mould such that a user knows how the tissue material is oriented relative to the cutting blades of the microtome. A user can hereby exert influence on the orientation of the tissue material cut into sections, and thus on the reliability and accuracy of the analysis of the tissue material.

In a further embodiment, the retainer comprises engaging means. This reduces the risk of the location and orientation of tissue material placed in the receiving space of the mould changing during for instance embedding thereof with a matrix material. The engaging means particularly comprise a plurality of pins extending from the retainer for the purpose of supporting tissue material on and/or between the pins. A retainer which is simple to produce is hereby provided, wherein the pins provide a user with the option of having the pins engage tissue material in many possible orientations relative to the retainer.

The retainer can be manufactured from diverse materials. What is important is that the material is flexible and cuttable with a microtome and that at least during preparation and study of tissue material the material is resistant to stains, solvents and chemicals used to prepare tissue material. A particularly suitable retainer is found to be manufactured substantially from a silicone rubber and/or hydrogel. Such materials not only have the above stated properties but can also be readily shaped and are homogenous, thereby reducing the risk of a user being distracted or becoming confused during study of prepared tissue material.

The invention also provides an assembly of a mould according to the invention and an enclosing element coupled to the mould. For the advantages of the assembly according to the invention reference is made to the mould according to the invention as described above.

In an embodiment, the enclosing element comprises a wall part. For the purpose of allowing passage of liquid the wall part can comprise a liquid-permeable film. The wall part can also be provided with a plurality of through-openings in distributed arrangement. Such a wall part is simple to produce and is strong, can be manufactured from diverse materials and is particularly manufactured substantially from a material selected from the group consisting of: metal, metal alloy, in particular steel, steel alloy, aluminium, aluminium alloy, plastic and combinations thereof. Such materials combine good strength and inertness and can be readily processed.

In a further embodiment, the wall part is provided, in the position substantially closing the opening liquid-permeably, with standing walls on the side remote from the receiving space, which standing walls enclose a space. A space is hereby obtained for receiving matrix material. The risk of matrix material coming to lie at undesirable locations during embedding of the tissue is hereby reduced. The space for receiving matrix material can also be at least partially filled with the matrix material. This strengthens the connection of the embedded tissue material to the liquid-permeable wall part in that a mechanical anchoring of the embedded tissue material to the liquid-permeable wall part is obtained. A strong connection of the embedded tissue material and the liquid-permeable wall part is advantageous when the liquid-permeable wall part is used to hold the embedded tissue material during cutting of the tissue material into sections.

In order to trace the tissue material back to the different sources of the tissue material, in a further embodiment the mould and/or the wall part are provided with at least one information surface for arranging data. Since large quantities of tissue samples are generally studied and analysed in laboratories, there is the risk that the origin of the tissue material can no longer be traced. By providing the mould and/or the wall part with at least one information surface for arranging data the origin of tissue material can be traced back at least in improved manner to the gonad-stimulating hormone from which it originates. This can for instance be a number linked to labels in a logbook, a database or a registration number of a patient. These numbers can for instance be arranged by hand using a pen. The information surface can also be made from a material which can be discoloured by electromagnetic radiation, wherein the material which can be discoloured by electromagnetic radiation comprises a radiation-absorbing pigment. The radiation-absorbing pigment can here comprise at least one of the following components: mica, pearl pigment, kaolin, aluminium metal, aluminium silicate, antimony trioxide, iron oxide, tin oxide, titanium oxide and aluminium hydroxide.

BRIEF DESCRIPTION OF THE DRAWINGS

The invention will be elucidated on the basis of non-limitative exemplary embodiments as shown in the following figures. Herein:

FIG. 1b is a side view of the mould according to FIG. 1a.

FIG. 2 is a perspective view of the mould according to FIG. 1a.

FIG. 4b is a side view of the assembly according to FIG. 4a.

DETAILED DESCRIPTION

Figure 1A:
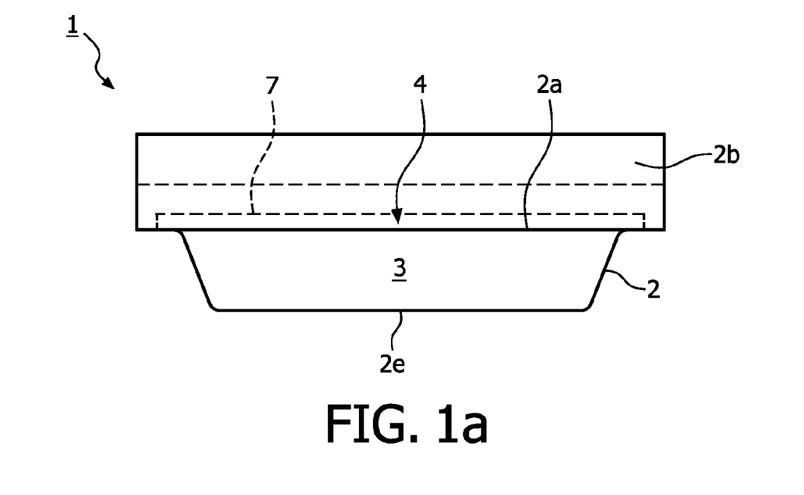
FIG. 1a is a front view of a mould according to the invention.
Figure 1B:
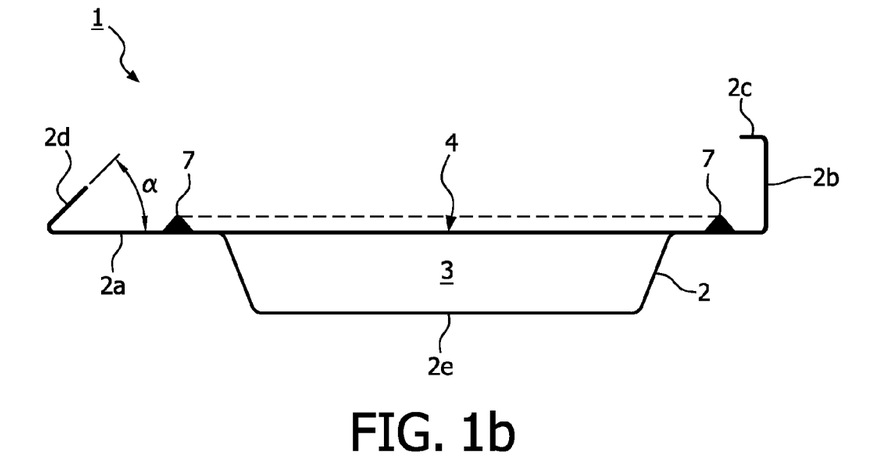
Figure 2:
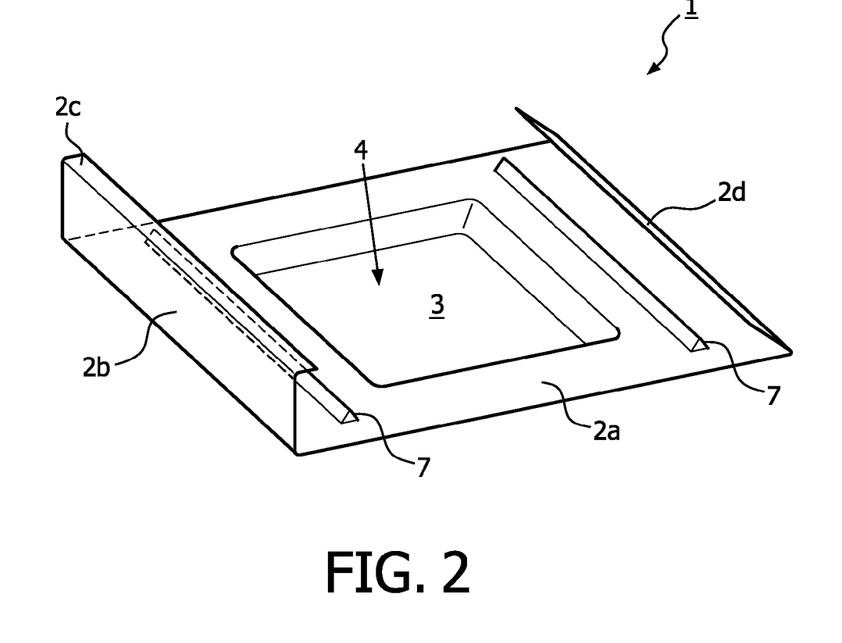

Referring to FIGS. 1a and 1b, a mould for holding tissue material designated in its entirety with 1 is shown. Mould 1 comprises an integrally formed housing 2 which is manufactured from a polyoxymethylene (POM) and which is provided with a receiving space 3 for the tissue material. Housing 2 also comprises an opening 4 (see also FIG. 2) for placing the tissue material in receiving space 3. Housing 2 comprises a flat wall part 2a which connects to opening 4 and which encloses the opening 4. Housing 2 comprises on a first side 1a of mould 1a first standing wall 2b extending from the flat wall part 2a, wherein the standing wall 2b is provided on the free end thereof with a flange 2c. On a second side 1b of mould 1 the mould 1 comprises a second standing wall 2d, wherein the second standing wall encloses an angle α with the flat wall part 2a, wherein the angle α is about 45°. Also connected to the flat wall part 2a are two protrusions 7 which extend along receiving space 3 and form a stop for an enclosing element 6 to be coupled to mould 1. Flange 2c and the second standing wall 2d hereby form two coupling means lying at a mutual distance for coupling enclosing element 6 to mould 1 for the purpose of enclosing the tissue material liquid-permeably in receiving space 3 (see FIGS. 4a and 4b). For this purpose opposite edges of enclosing element 6 extend respectively between the second standing wall 2d and the flat wall part 2a and between flange 2c and flat wall part 2a (see FIGS. 4a and 4b). Enclosing element 6 rests here on protrusions 7. An enclosing element 6 coupled in such a manner to mould 1 ensures that displacement of tissue material held in enclosing space 3 through opening 4 and outside receiving space 3 is prevented. Although enclosing element 6 is not precluded from being under bias respectively between the second standing wall 2d and the flat wall part 2a and between flange 2c and flat wall part 2a, in the embodiment shown here the enclosing element is received movably relative to housing 2 of mould 1. A bottom 2e of receiving space 3 can also be given a liquid-permeable form here, for instance by providing the bottom 2e with a plurality of through-openings arranged in the bottom 2e. Liquid carried into the receiving space can hereby be discharged through the liquid-permeable bottom 2e.

Figure 3:
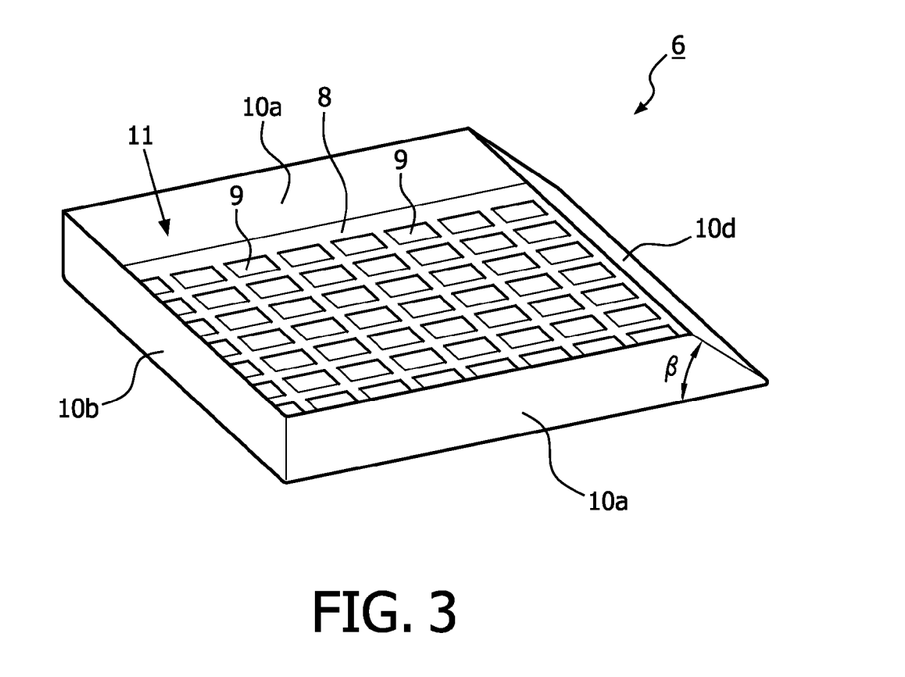
FIG. 3 is a perspective view of an enclosing element in accordance with the assembly of FIGS. 4a and 4b.

Referring to FIG. 3, an enclosing element 6 manufactured substantially from polyoxymethylene (POM) is shown. Enclosing element 6 comprises a wall part embodied as bottom 8, wherein the bottom 8 is provided with a plurality of through-openings 9 in distributed arrangement. Standing walls 10a, 10b, 10c, 10d connect to bottom 8, the standing walls 10a, 10b, 10c, 10d enclosing a space 11. Standing walls 10a, 10b, 10c extend here transversely of bottom 8 and standing wall 10d encloses an angle β with bottom 8, wherein the angle β is about 45°. Enclosing element 6 comprises an information surface for arranging data formed by standing wall 10d. Standing wall 10d is manufactured for this purpose from a material which can be discoloured by electromagnetic radiation, wherein the material which can be discoloured by electromagnetic radiation comprises aluminium silicate for the purpose of absorbing radiation.

Figure 4A:
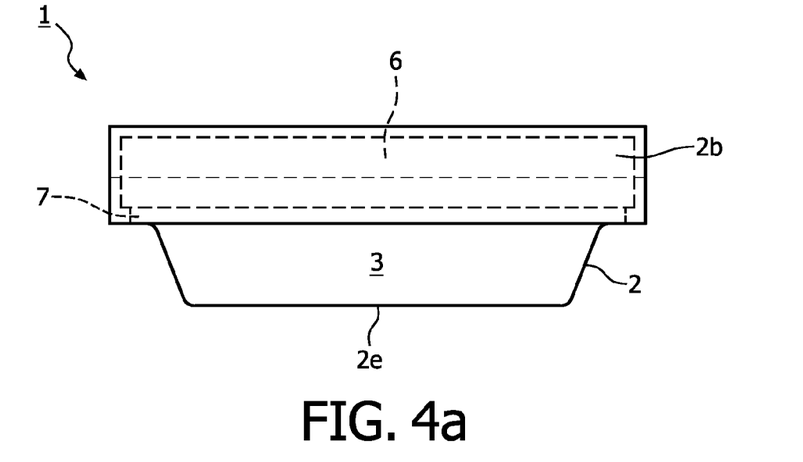
FIG. 4a is a front view of an assembly of a mould according to the invention and an enclosing element coupled to the mould.
Figure 4B:
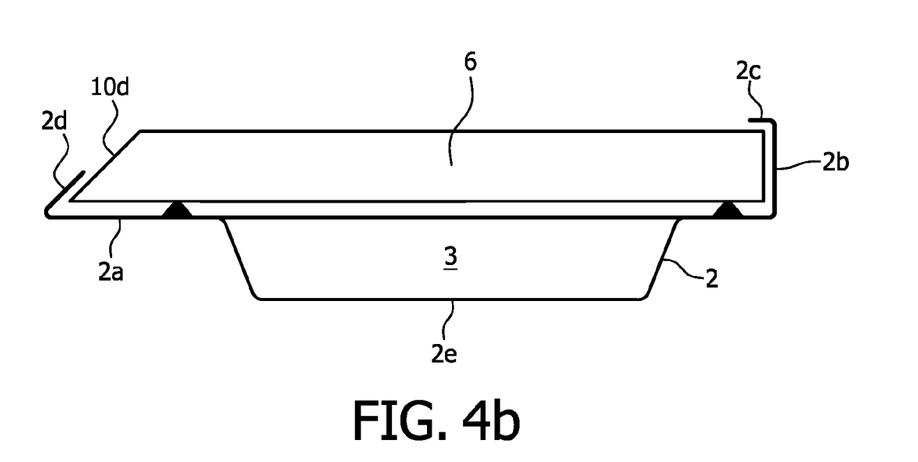

Referring to FIGS. 4a and 4b, an assembly is shown of a mould 1 according to FIG. 1a and an enclosing element 6 according to FIG. 3 coupled to mould 1.

Preparation of the tissue material proceeds as follows:

In the embodiment shown here, a quantity of tissue material isolated from a human body, such as a tumour tissue, is placed in receiving space 3 of mould 1. Material isolated from for instance animals or plants can however also be placed in receiving space 3 of mould 1. Enclosing element 6 is then coupled to mould 1. The standing wall 10d of enclosing element 6 is placed for this purpose between the flat wall part 2a and the second standing wall 2d. Enclosing element 6 is coupled to the mould as shown in FIGS. 4a and 4b by carrying standing wall 10b of enclosing element 6 in the direction of flange 2c and urging it under flange 2c by elastically deforming flange 2c and the standing wall 2b of mould 1. The enclosing element rests here on protrusions 7. The tissue material placed in receiving space 3 is enclosed here in receiving space 3 in the position closing the opening 4 liquid-permeably by the enclosing element 6 coupled to mould 1. Water is extracted from the tissue material by subsequently guiding mould 1, provided with tissue material enclosed in receiving space 3, through a hydrophilic liquid such as an alcohol solution. The level of the hydrophilic liquid relative to mould 1 is preferably lowered and raised repeatedly here, wherein the tissue material is repeatedly situated respectively substantially above and below the level of the hydrophilic liquid. During the lowering and raising of the level of the hydrophilic liquid relative to the tissue material the receiving space 3 of mould 1 respectively faces at least partially downward and upward. Air present in the tissue material will hereby escape from the tissue material, whereby the extraction of water takes place in improved manner, i.e. in a shorter period of time in which a larger quantity of water is extracted. After extraction of water from the tissue material the receiving space 3 is filled with paraffin, by having the paraffin flow through the bottom 8 of enclosing element 6, which is provided with a plurality of through-openings 9 in distributed arrangement and is thus liquid-permeable, into receiving space 3, whereby the tissue material which is placed in receiving space 3 and from which water has been removed is embedded with paraffin. For this purpose the paraffin can be fed in simple manner through the enclosing element 6 coupled to mould 1 and into receiving space 3. The space 11 enclosed by the standing walls 10a, 10b, 10c, 10d is here also at least partially filled with paraffin. The paraffin present in receiving space 3 and the space 11 enclosed by standing walls 10a, 10b, 10c, 10d here forms one whole and thereby makes a mechanically anchored connection to enclosing element 6.

The tissue material is hereby prepared and can be further processed. The tissue material must for this purpose be cut into sections. This can be done in simple manner as follows. Enclosing element 6 is uncoupled from mould 1, wherein the paraffin present in receiving space 3 and the space 11 enclosed by standing walls 10a, 10b, 10c, 10d, and thereby the tissue material, is likewise released from mould 1. By then engaging enclosing element 6 with a cutting device, preferably on one or more standing walls 10a, 10b, 10c, the tissue material can be easily cut into sections. Because standing wall 10d is provided with an information surface, data of the tissue material are coupled to the tissue material during preparation and cutting thereof into sections. This decreases or even reduces to zero the risk of the origin of the tissue material no longer being traceable.

Figure 5A:
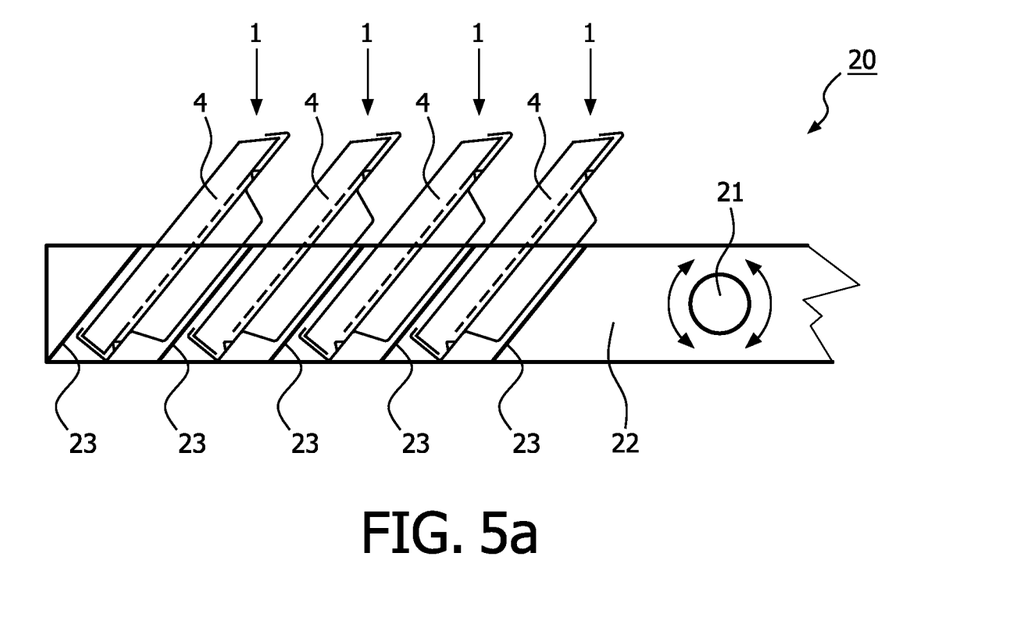
FIG. 5a is a side view of a rack for holding a plurality of moulds of a device for preparing tissue material according to the invention, wherein the rack is oriented such that the openings of the moulds face upward.

Referring to FIG. 5a to FIG. 5e, a rack 20 is shown which is connected for rotation about a shaft 21 to a frame (not shown) of a device, not further shown in detail, for preparing tissue material. Rack 20 is manufactured from plastic and comprises two side walls 22, between which holder elements 23 extend. Between holder elements 23 can be placed moulds 1 (moulds 1 are according to the invention and therefore provided with enclosing elements) for holding moulds 1 between holder elements 23. The rack 20 provided with moulds 1 is placed in a container 24 for pretreatment liquids, this such that rack 20 is rotatable about the shaft 21. The device is provided for this purpose with drive means such as a drive motor. The horizontal orientation of rack 20 shown here provides for an oblique orientation of moulds 1 relative to the horizontal direction. This orientation is appropriate when the level of the pretreatment liquid in the container 24 is raised from the bottom of the container 24 to beyond the horizontal level of rack 20. In this way air possibly present in the tissue can displace upward through the liquid and out of the tissue during filling of the container 24 with pretreatment liquid. In FIG. 5a the moulds are oriented at an angle to the horizontal direction of about 45°.

Figure 5B:
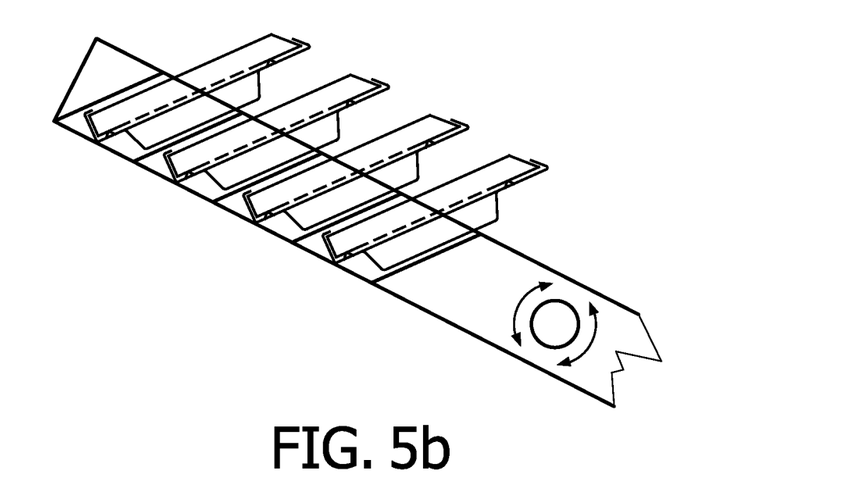
FIG. 5b is a side view of the rack of FIG. 5a, wherein the rack is oriented such that the openings of the moulds likewise face upward.

In the orientation shown in FIG. 5b, rack 20 is rotated in clockwise direction around shaft 21 through a predetermined arc relative to the orientation shown in FIG. 5a. In the orientation shown in FIG. 5c rack 20 is rotated in counter-clockwise direction around shaft 21 through a predetermined arc.

Figure 5C:
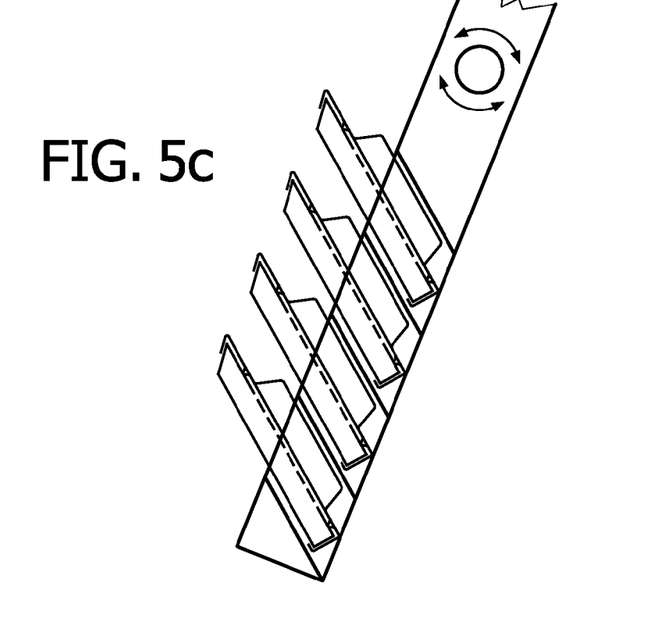
FIG. 5c is a side view of the rack of FIG. 5a, wherein the rack is oriented such that the openings of the moulds face downward.

In the orientation shown here hydrophilic liquid can penetrate easily into the tissue placed in mould 1.

Figure 5D:
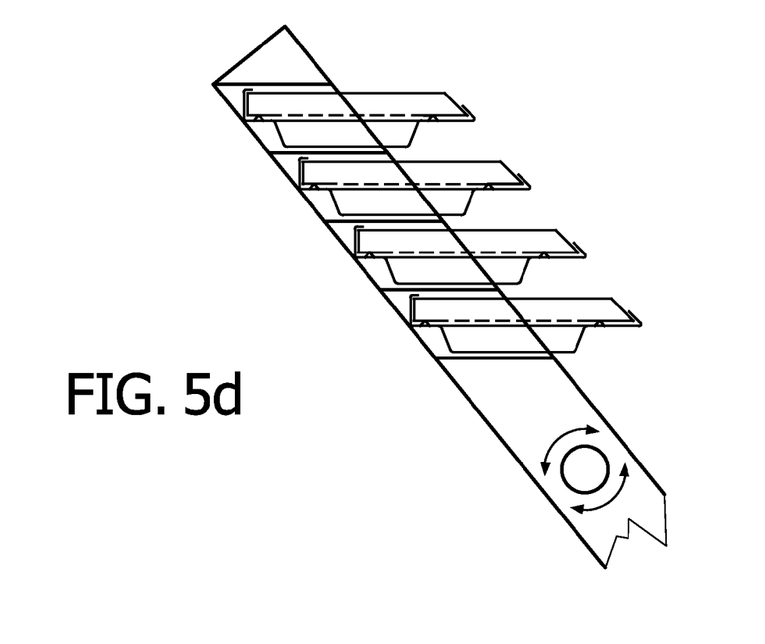
FIG. 5d is a side view of the rack of FIG. 5a, wherein the rack is oriented such that the openings of the moulds face upward and wherein the moulds extend substantially horizontally.
Figure 5E:
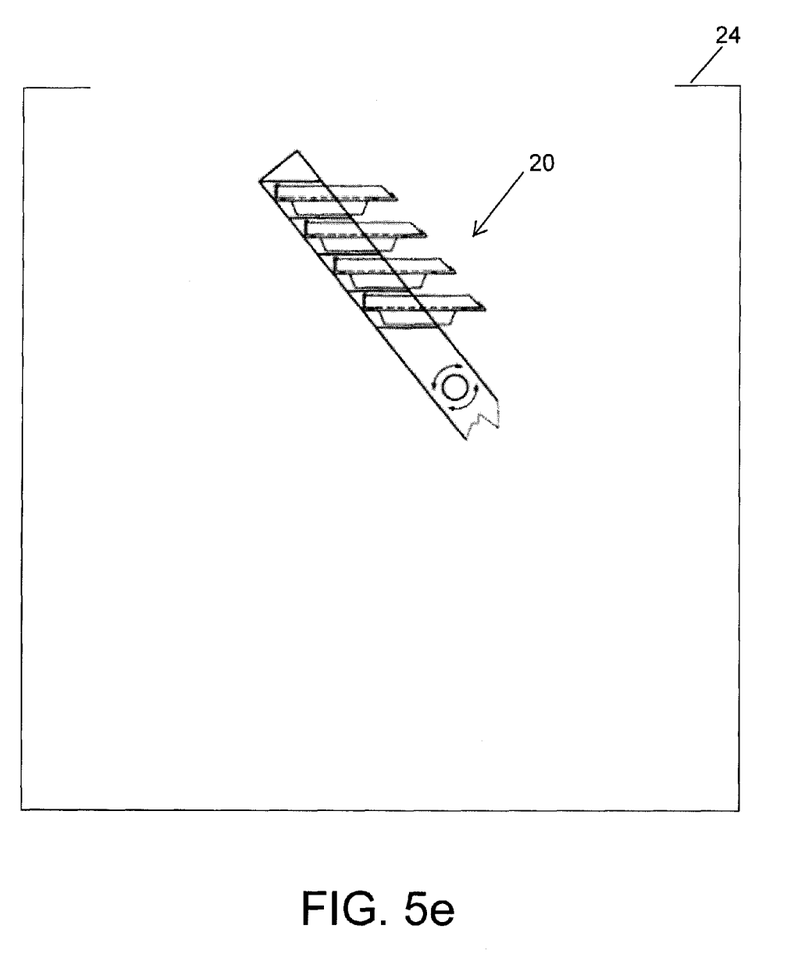
FIG. 5e is a side view of the rack of FIG. 5a, wherein the rack is positioned within the container such that the openings of the moulds face upward.

In the orientation shown in FIG. 5d rack 20 is rotated in clockwise direction around shaft 21 relative to the orientation shown in FIG. 5a such that the mould extends substantially horizontally, wherein openings 4 of moulds 1 face upward. In the orientation shown here moulds 1 can be filled in simple manner with paraffin for the purpose of embedding the tissue from which water has been extracted. When moulds 1 have been filled with paraffin, moulds 1 can be taken out of rack 20, after which the paraffin is cooled.

To enable cutting of sections the housing is separated from the enclosing element saturated with paraffin, wherein the tissue material likewise embedded in paraffin remains attached to the enclosing element and is secured with the enclosing element in the microtome apparatus.

It will be apparent that the invention is not limited to the exemplary embodiments shown and described here, but that within the scope of the appended claims numerous variants are possible which will be self-evident to the skilled person in this field. It is thus possible for instance to arrange a plurality of racks in the holder which are each rotatable around a horizontal shaft.

The method and device according to the invention make it possible to prepare tissue material in a single device, wherein it is no longer necessary to take pretreated tissue material out of a holder and place it in a mould. By providing an assembly of a mould and a closing element for the mould which is permeable to liquids, more specifically treatment liquids, it now becomes possible to give tissue material enclosed in the mould a pretreatment and to embed it in a matrix material without the tissue material leaving or having to leave the mould.

The invention claimed is:

1. Device for preparing tissue material by contacting the tissue material with a liquid, the device, comprising a liquid container configured to receive said liquid;
   a carrier for carrying at least one assembly of a mould and an enclosing element coupled thereto; and
   a shaft;
   wherein the mould comprises a housing provided with a receiving space for the tissue material and an opening for placing the tissue material into the receiving space, and coupling means for coupling the enclosing element to the mould, the enclosing element being adapted for enclosing the tissue material liquid-permeably in the receiving space, wherein the carrier is rotatable around the shaft to adjust the orientation of the carrier in the liquid container; and
   wherein the device further comprises means for varying the level of said liquid in the liquid container.

2. Device as claimed in claim 1, wherein the device is adapted to translate liquid held in the liquid container and the carrier relative to each other.

3. Device as claimed in claim 1, comprising a carrier in which a number of assemblies of mould and enclosing element can be received, wherein the carrier is rotatable about a preferably horizontal shaft.

4. Device as claimed in claim 1, comprising means for guiding tissue material placed in the receiving space of said mould through the liquid in the liquid container.

5. Device as claimed in claim 1, comprising means for exchanging a first liquid in the liquid container with a second liquid that differs from the first liquid.

6. Device as claimed in claim 5, wherein the first liquid comprises a pretreatment liquid for extracting water from the tissue material, and the second liquid comprises a matrix material for embedding the tissue material.

7. Device as claimed in claim 1, wherein the means for varying the level of the liquid are adapted to repeatedly raise and lower the level of the liquid in the container such that the tissue material repeatedly lies above and below the level of the liquid.

8. Device as claimed in claim 7, wherein the shaft is adapted to position a mould with its enclosing element facing at least partially downward during lowering the level of the liquid in the container, and at least partially upward when raising the level of the liquid in the container.

9. Device as claimed in claim 7, wherein the shaft is adapted to position a mould with its enclosing element under an oblique angle relative to the horizontal direction when the level of the liquid in the container is raised.

10. Device as claimed in claim 9, wherein the oblique angle is larger than 45°.

11. Device as claimed in claim 7, wherein the shaft is adapted to position a mould with its enclosing element substantially vertical when the level of the liquid in the container is lowered.

12. Device as claimed in claim 7, wherein the shaft is adapted to position a mould with its enclosing element substantially horizontal when a first liquid in the liquid container is exchanged with a second liquid that differs from the first liquid.

* * * * *